US006420123B1

United States Patent
Furka

(12) 
(10) Patent No.: US 6,420,123 B1
(45) Date of Patent: Jul. 16, 2002

(54) SPATIALLY DEFINED SYNTHESIS

(76) Inventor: Arpad Furka, Csengery U.23, Budapest (HU)

( * ) Notice: Subject to any disclaimer, the term of this patent is extended or adjusted under 35 U.S.C. 154(b) by 0 days.

(21) Appl. No.: 09/544,411

(22) Filed: Apr. 6, 2000

Related U.S. Application Data

(60) Provisional application No. 60/127,944, filed on Apr. 6, 1999.
(51) Int. Cl.⁷ .............................................. G01N 33/53
(52) U.S. Cl. ......................................... 435/7.1; 530/334
(58) Field of Search .................... 436/518; 530/334; 435/4, 7.1

(56) References Cited

U.S. PATENT DOCUMENTS 5,639,603 A    6/1997   Dover et al. .................... 435/6

OTHER PUBLICATIONS

Gallop et al. Applications of combinatorial technologies to drug discovery. Background and peptide combinatorial libraries. J. Med. Chem. 37:1233–1241. 1994.
Rapp. Macrobeads a microreactors: new solid –phase synthesis methodology, In Combinatorial Chemistry: synthresis and applications. Wilson RS, Czarnick AW Eds. John Wiley and Sons. pp. 65–94. 1997.

*Primary Examiner*—Padmashri Ponnaluri
*Assistant Examiner*—Thomas Prasthofer

(57) ABSTRACT

In accordance with the method of the invention and within the framework of the split synthesis technique, compounds are synthesized on macroscopic solid support units which are spatially organized in groups, referred to herein as strings, so that the location of each unit in a string is known and recorded. Each string is placed in a reaction vessel for contact with a suitable reagent or reagents to couple a first component on the support units. Each string is submitted to a different reaction and the sequential arrangement of the support units is maintained throughout the whole reaction step and any subsequent washing steps. At the completion of a reaction step the support units of the strings (referred to as source strings) are sorted in a different sequential arrangement to form new strings (referred to as destination strings) for the next reaction step. The reorganization of the support units into new destination strings is recorded for each reaction step in the synthesis. The destination strings may then be converted to source strings by subjecting each string to different second reaction steps to couple another component onto the solid support units. The reaction and sorting steps are repeated until the desired products are formed. The sequence history is reviewed and the composition of each product is predicted without the need for tags or labels. The sorting steps can be carried out manually or preferably by automated means.

12 Claims, 8 Drawing Sheets

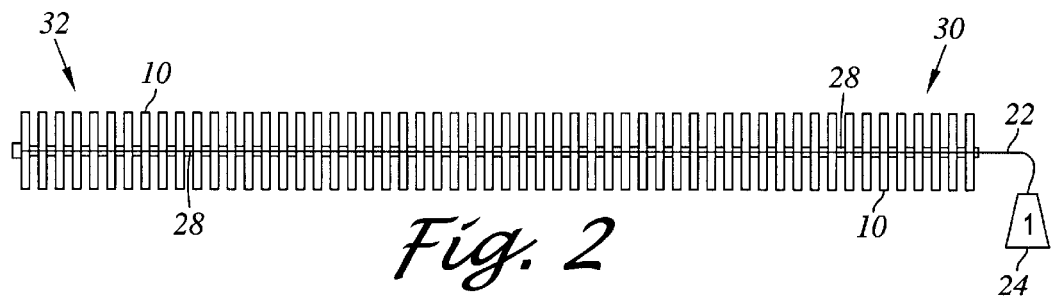
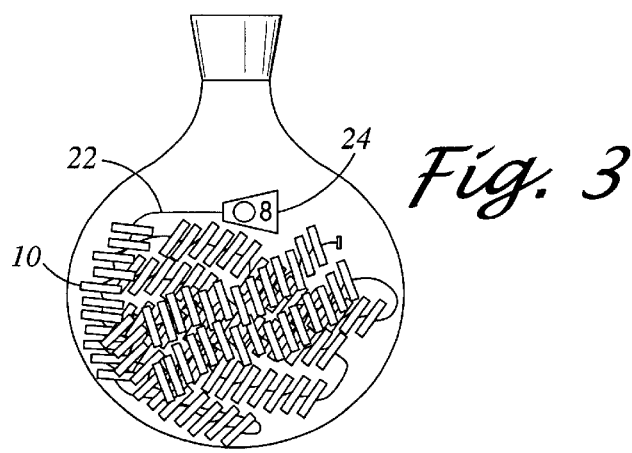
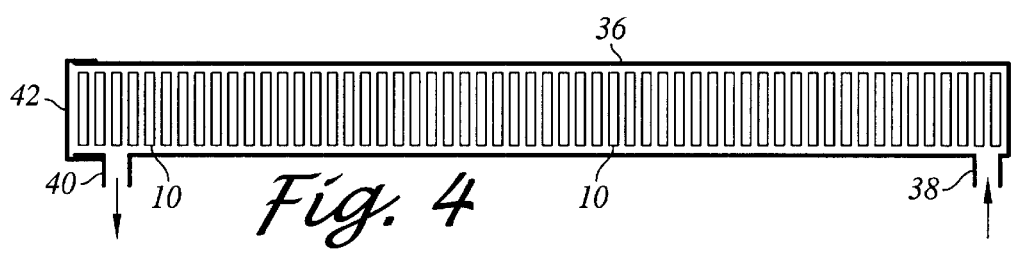
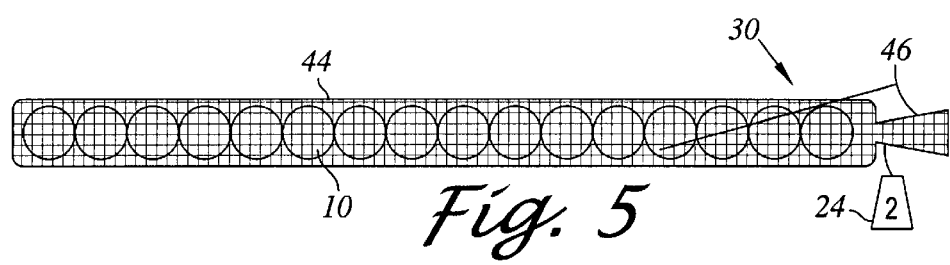

SERIAL SORTIG
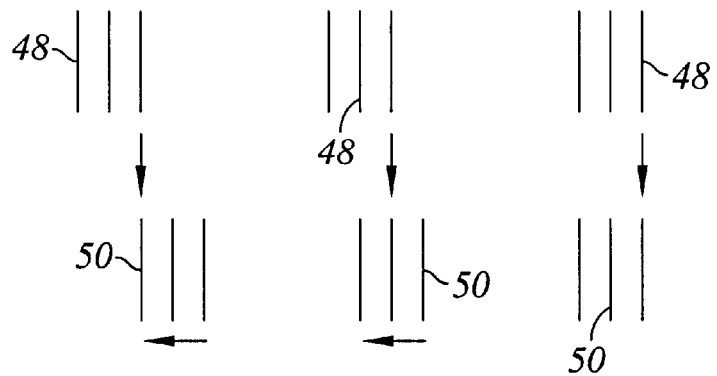
SEMI-PARALLEL SORTING
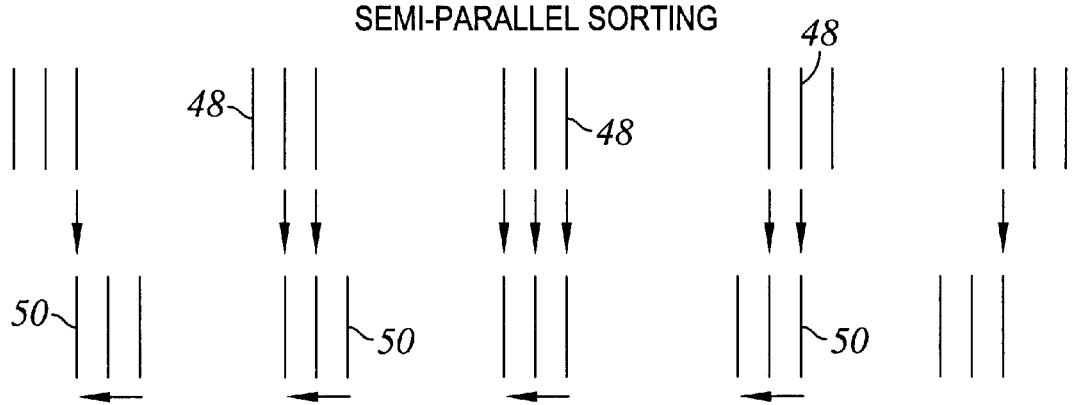
PARALLEL SORTING
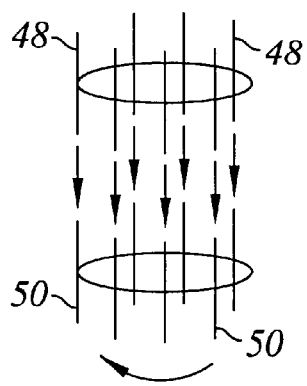
Fig. 6

SPATIALLY DEFINED SYNTHESIS

CROSS REFERENCE TO RELATED APPLICATIONS

This application claims the benefit of the filing date of Provisional Application Serial No. 60/127,944, filed Apr. 6, 1999, in the name of Ápad Furka.

FIELD OF THE INVENTION

This invention relates to solid phase synthesis of chemical compounds and more particularly to a synthesis method employing support units arranged in groups of known spatial organization of the support units.

BACKGROUND OF THE INVENTION

The split synthetic method (originally called portioning-mixing) introduced by Furka and his colleagues in 1988 made it possible to prepare millions of compounds in a few days. Furka, Á.; Sebestyén, F.; Asgedom, M, Dibó, G. In *Highlights of Modern Biochemistry, Proceedings of the 14th international Congress of Biochemistry*, VSP. Utrecht, The Netherland; 1988, Vol. 5, p 47; Furka, Á.; Sebestyen, F.; Asgedom, M.; Dibó, G. In *Abstracts of 10th International Symposium of Medicinal Chemistry*, Budapest, Hungary, 1983, p 288.

The method is based on the solid phase synthetic procedure introduced by Merrifield. The new method was demonstrated with the synthesis of peptide mixtures called peptide libraries. Each cycle of the solid phase synthesis was replaced by the following operations:

(i) Portioning of the solid support into equal samples;

(ii) Coupling a different amino acid to each sample;

(iii) Mixing the samples;

These operations were repeated until the desired length of the peptides was achieved. The synthesized peptides could be used either as real mixtures after cleaving them from the support, or in tethered form by removing only the protecting groups. The latter approach took advantage of the fact that in the split synthesis only a single compound forms on each bead (and not a mixture).

Lam et al. developed a method for screening the libraries in tethered form. Lam, K. S.; Salmon, S. F.; Hersh, F. M.; Hruby, V. J.; Kazmierski, W. M.; Knapp, R. J. Nature 1991, 354, 82. The bead carrying the bioactive peptide could easily be identified by its color and, after manually picking it out, the sequence could be determined by submitting the bead to sequencing. Later the split method was applied for preparing libraries of non-peptidic small organic molecules. Since, the identification of the structure of the majority of organic compounds is not as easy as determining the sequence of peptides, different encoding methods were developed. The code attached to each bead in the course of synthesis in parallel with the product forming reactions, preserved the synthetic history of each bead. Based on the synthetic history, the identity of the compound carried by the bead could easily be deduced. Sequences of peptides (Nikolaiev et al. *Pept Res.* 1993, 6, 161 (1993)) and those of oligonucleotides (Brenner et al. *Proc. Nati. Acad. Sd. USA*, 89, 5381 (1992)) were suggested for coding. A non-sequential encoding procedure was introduced 1993 by Ohhmeyer et al. This "binary" coding method is successfully used even nowadays.

The high-throughput screening methods applied in the majority of pharmaceutical companies are based on testing individual compounds. Although the split method does produce individual compounds, the quantity present on a single bead is too low and not enough compound is produced to make multiple tests and repetitions. In addition, the identity of the compound belonging to any bead has to be identified by experimentally determining the code. Despite the high synthetic efficiency of the split method, most of the pharmaceutical companies prefer to use automated parallel synthesis methods for preparation of their combinatorial libraries. By these methods each compound is produced in several milligram quantities. The parallel synthesis, however, is slow and expensive. For this reason efforts have been made to combine the high efficiency of the split synthesis with the advantage of the parallel method in producing the new compounds in higher quantities.

The high efficiency of the split synthesis is a result of the fact that in a reaction step carried out with a single reagent, thousands or even millions of new compounds may form in microscopic beads of the solid support. In order to be able to produce the new compounds in milligram quantities, the microscopic individual beads have to be replaced by their macroscopic assemblies enclosed in permeable bags or capsules. These macroscopic synthetic units have to be redistributed among the reaction vessels before each synthetis step according to the rules of the split synthesis. In order to be able to do this, and to make possible the identification of the formed compound, the bags or capsules have to be labeled. Even in this case redistribution of thousands of bags or capsules takes too long time. In one of the methods developed to solve the problem, a microchip is enclosed into each capsule (Nicolaou et al. *Angew. Chem. Int. Ed. Engl,* 36, 2289. (1995)) which stores an electronic code. The capsules are pooled after each synthetic step and fed into an automatic machine constructed for sorting the capsules. In the sorting process first the electronic codes are determined, then the capsules, one at a time, are automatically delivered into their destination reaction vessels. Sorting of 10,000 capsules takes about 10 hours.

In another solution, small ceramic plates are applied, which are grafted on their surface with derivitized polystyrene. The plates are labeled by a two dimensional visual code etched by laser onto the ceramic support (Xiao et al. *Angew. Chem. Int. Ed. Engl.,* 36,780. (1997)). Again the code is readable by the sorting machine.

SUMMARY OF THE INVENTION

The present invention is designed to preserve those operations of the split synthesis technique which are important for the high efficiency, i.e. splitting before coupling and coupling the reagent to many properly grouped macroscopic units. Mixing or pooling is omitted, since this operation is required only when working with small independent beads as solid support, to make a near homogenous mixture before the split operation. In the present invention a radically new method is introduced to put the above principles into practice.

In accordance with the method of the invention and within the framework of the split synthesis technique, compounds are synthesized on macroscopic solid support units which are spatially organized in groups, referred to herein as strings, so that the location of each unit in a string is known and recorded. Each string is placed in a reaction vessel for contact with a suitable reagent or reagents to couple a first component on the support units. Each string is submitted to a different reaction and the sequential arrangement of the support units is maintained throughout the whole reaction step and any subsequent washing steps. At the completion of a reaction step the support units of the strings (referred to as source strings) are reorganized into a different sequential arrangement to form new strings (referred to as destination strings) for the next reaction step. The reorganization of the support units into new destination strings is recorded for each reaction step in the synthesis. The destination strings may then be converted to source strings by subjecting each string to different second reaction steps to couple another component onto the solid support units the reaction and sorting steps are repeated until the desired products are formed. The sequence history is reviewed and the composition of each product is predicted without the need for tags or labels. The reorganization step, which is referred to herein as sorting, can be carried out manually or preferably by automated means.

The support units are formed of suitable materials which carry functional groups for the attachment of the first building block of the compound being formed. Methods for functionalizing materials for solid support reactions are well understood in the art. The support units may be formed into various shapes to ensure maximum contact with the reagents.

In one embodiment of the invention the support units are disk shaped with a center opening. In this embodiment the support units are retained in their position in the string by arrangement on an elongated flexible retainer, such as a string or cord, which extends through the center openings of the support units. The support units are reorganized after reaction by moving the support units in a predetermined pattern, referred to as pattern sorting, from their source strings onto new destination strings or cords. In a modification of this embodiment the support units are formed on Chiron crowns that comprise a stem and a depending crown portion. The crown portion is derivitized for coupling the first building block of the compounds being synthesized. Chiron crowns are commercially available and do not per se form a part of this invention.

In another embodiment the support units comprise conventional resin beads confined within a capsule or porous bag. The capsules and porous bags are readily adapted for easy sorting during the reorganization step.

BRIEF DESCRIPTION OF THE DRAWINGS

FIG. 2 illustrates a string of support units;

FIG. 3 shows the string of support units of FIG. 2 in a reaction vessel;

FIG. 4 illustrates a tubular reaction vessel in which are disposed support units for coupling reaction;

FIG. 5 illustrates another embodiment in which support units are retained in a mesh bag;

FIG. 6 is a schematic representation of three sorting patterns for redistributing support units for a coupling reaction;

DETAILED DESCRIPTION OF THE INVENTION

As used herein the term "spatial" refers to the location or sequence of a support unit relative to the other support units in a string. The spatial location of each support unit in a string is recorded, preferably by computer, so that upon completion of all of the reaction steps the location history of each support unit the respective strings are traced and the structure of the compound formed on the support units is known without the necessity of sequencing analysis or the use of markers.

In carrying out the method of this invention the individual support units are spatially arranged in strings of support units for submission to a reaction vessel to attach the initial building block or segment of the compounds being formed. Upon completion of the first reaction, the support units are redistributed to form new destination strings for attachment of the next building block of the compound. The redistribution is carried out in a predetermined pattern, for example, within the limits of the split principle. Three of such patterns, described below, are referred to as serial sorting, parallel sorting and semi-parallel sorting. It will be understood, however, that other patterns may be used to form combinatorial libraries and the like.

Figure 1A:
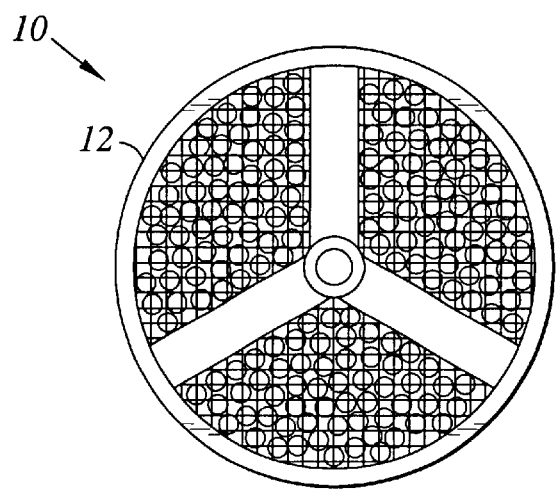
FIG. 1A and FIG. 1B illustrate several forms of support units utilized in the method of the invention.
Figure 1B:
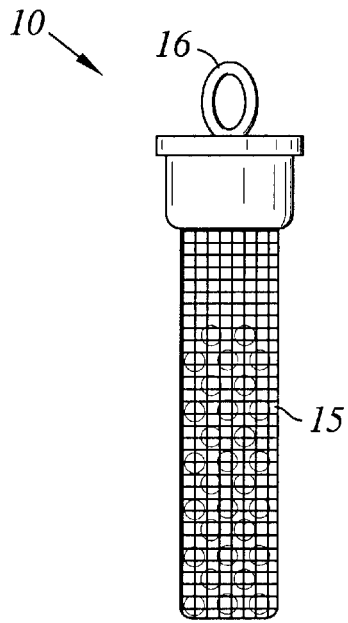
Figure 1C:
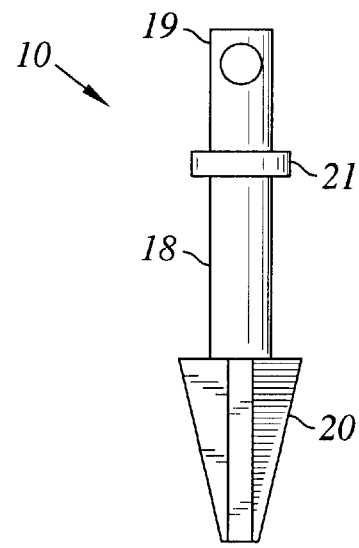
FIG. 1C illustrates a single crown stem.

The support units comprise conventional solid supports, such as Merrifield or Wang solid supports, that do not per se form a part of the present invention. The support units may be formed into shapes or contained in a porous container for arrangement in strings. Thus, the support unit may consists of a solid polymer disc with a hole in its center or a solid ball. The surface of the polymer is grafted with a properly functionalised. As shown in FIG. 1A, the support unit 10 may consist of a disk shaped capsule 12 having a porous face and means for retaining the support unit, such as a center hole 14 through the disk (FIG. 1A) or an elongated, vial shaped 15 (FIG. 1B) having porous surfaces and a tab 16 with a hook or hole for retaining the support unit. Conventional resin beads 14 are contained in the either capsule 12. Another configuration which is used with good results is the resin crown 17 (FIG. 1C). The crowns consist of an elongated stem 18, one end of which defines a hook or hanger 19, such as by having a hole formed in the stem, and the opposite end defining a resin crown 20 which is derivitized for coupling product segments. Preferably, a collar 21 is formed on the stem 18 adjacent the hanger 19 for supporting the crown in a slotted sorting tray as will be described below.

The particular configuration of the support unit 10 is not critical and the choice of support unit configuration is a matter of choice depending upon the sorting equipment and type of coupling reactions to be carried out. It is essential, however, that the configuration of the support unit be such as to permit access to at least the surfaces of the support units by the reagent in the available reaction vessels.

The strings are comprised of a series of spatially arranged support units 10 carried or supported by a retainer for maintaining the support units in their spatial arrangement throughout a complete reaction step, including all necessary washing steps. FIG. 2 illustrates one embodiment of the invention in which the support units 10 are disk shaped and are maintained on a flexible cord retainer 22. Preferably the ends of the flexible cord are looped back and tied together to retain the support units on the cord. Optionally spacer elements 28 are positioned between each of the disks to insure that the reactants are able to reach the derivitized interior surfaces of the disks during the coupling operation. An identifying tag 24 is secured at one end of the string designated as the "head" 30 of the string. Alternatively, a full stem 18 from a crown painted in a distinctive color may be employed as the identifying tag 24 of a string of support units. A partial stem may be used at the end of the string opposite the tag end, designated the "tail" 32 of the string. The tag 24 serves both to identify the string and to designate the head 30 of the string in order to maintain the correct orientation of the string during the sorting steps. If the orientation of the support units 20 is not maintained throughout the entire synthesis of the combinatorial library the predictability of the product formed on the support units 20 will be lost and time consuming analysis will be required for product identification. Thus, it is essential during the sorting process described below, that the direction in which the support units 10 are sorted from the source strings to the destination strings be consistent through the entire synthesis process.

As shown in FIG. 3, the flexible cord retainer 22 permits the string to be immersed in a conventional reaction flask 34 during the coupling step and, when straightened out, the support units 10 are returned to their original spatial arrangement. The individual support units 10 are removed from their strings, referred to as the source strings, and transferred to a new strings, referred to as the destination string, during each sorting step. In addition to tagging the strings for identification, tagging also indicates the orientation of the string.

In another embodiment shown in FIG. 4, the disk shaped support units 10 are arranged in a closed tube 36 having an inlet port 38 and an outlet port 40 for the ingress and egress of reactants and washing fluids. A removable closure 42 seals one end of the tube during the reaction and is removed to allow the support units to be sorted into the next string. The tube serves both as a reaction flask and the retainer for the support units 10. The closure 42 defines the head 30 of the string and carries identifying indicia or is colored for identification of the string. In sorting, the closure 42 is removed and the support units 10 are transferred from the head 30 of the source string in the tube to form the destination string that is carried by a suitable retainer 22 such as a tray or rack. The support units are then transferred back into the tube 36 in the reverse direction so that the orientation of the units and the subsequent sorting direction is the same as in the original source string.

In the embodiment shown in FIG. 5, the support units 10 are of a round or ball shaped configuration. The ball shaped support units 10 are retained in an elongated porous bag 44 which has a tag on one end for identification and orientation purposes. The bag is open at one 46 to insert and remove the support units 10 and during the reaction step the open end is closed off by a suitable tie to tightly retain the support units in their spatial arrangement. The head 30 of the string is adjacent the open end and the tie carries a tag 24 to identify the string and its orientation.

Upon completion of each reaction step the support units 10 are rearranged from their source strings into new destination strings for a subsequent reaction step to couple the next monomer or unit in the product sequence. This step of the invention is referred to as "sorting". In sorting, the support units 10 are redistributed from the first reaction or source strings to new destination strings. The pattern redistribution is exemplified by three predetermined protocols, referred to as serial sorting, semi-parallel sorting and parallel sorting. It will be understood that the number of support units 10 is may be equal to the number of compounds to be prepared or may be a multiple of the number of compounds to be synthesized. For example, to double the quantity of each synthesized compound, one may simply assign two units for each compound to be synthesized thereby doubling the quantity produced.

Three basic types of sorting protocols are schematically illustrated in FIG. 6. The three types of sorting protocols illustrated are serial sorting, semi-parallel and parallel sorting. It will be understood, however, that these procedures may be modified and adapted depending \upon the chemistries involved in the synthesis. The source strings 48 and destination strings 50 containing the support units 10 are shown as straight lines.

Figure 7:
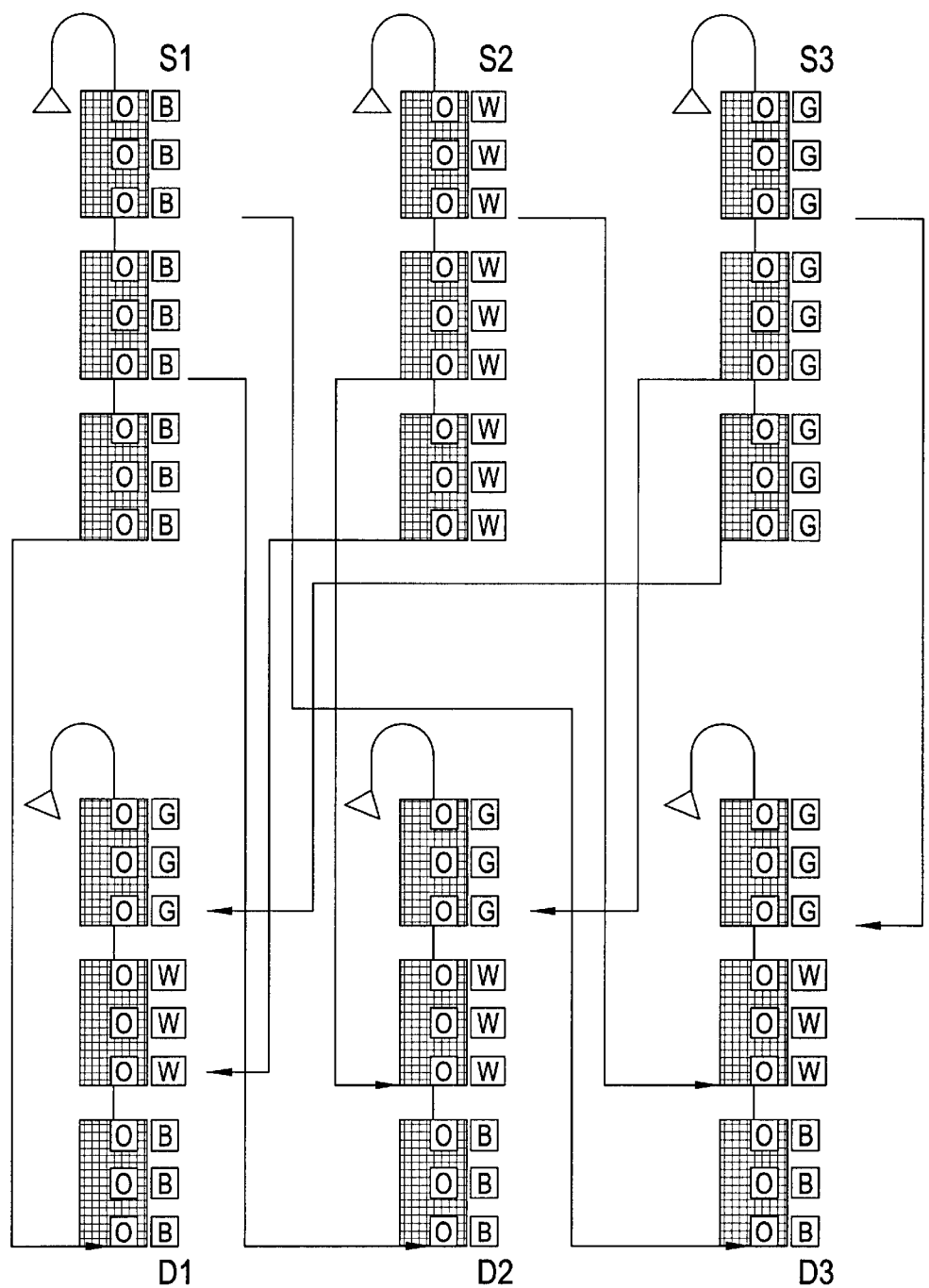
FIG. 7 is schematic representation showing strings of support units after the first coupling reaction and the first serial sort.

As illustrated in FIG. 6 and further in FIG. 7, in serial sorting all support units 10 of each of the source strings 48 are sequentially distributed among the destination strings 50 (this may involve several rounds of deliveries). This is followed by the sequential distribution of the support units from the next source string followed by the next until all support units 10 have been redistributed onto destination strings 50.

As shown in parallel sorting, the source strings 48 are aligned with destination strings 50 and deliveries of the support units 10 from the source strings are executed in parallel from each source string to the aligned destination string. The alignment is changed and the next set of support units 10 are transferred from the source strings 48 to the aligned destination strings 50. The realignment of source strings 48 and destination strings 50 is repeated until all of the support units 10 have been transferred to destination strings. Semi-parallel sorting involves serial sorting at the start and finish of the sorting protocol and parallel sorting during the intermediate sorting steps.

Parallel sorting is the most efficient sorting technique when the number of source strings 48 equals the number of destination strings 50. Preferably the strings are circularly arranged, for example on a carousel, which allows either the source strings 48 or the destination strings 50 to be rotated into a new alignment after each transfer of the support units.

In semi-parallel sorting, also illustrated schematically in FIG. 6, the deliveries of transfer groups of support units 10 also start with one source string. As the destination strings 50 are repositioned into alignment with the source strings, transfer blocks are transferred from each of the source strings 48 that are aligned with a destination string. As illustrated in FIG. 6 the destination strings 50 move right to left. There are five transfer positions in the illustration, i.e.(i) the right source string 48 aligned with the left destination string 50; (ii) the right and center source strings aligned with the left and the center destination strings; (iii) all three source strings aligned with all three destination strings; (iv) the left and the center source strings aligned with the center and the right destination strings; and (v) the left source string aligned with the right destination string. Accordingly, transfers can occur from one, two or three source strings 48 in a single position. For this reason semi-parallel sorting is more efficient than serial sorting where transfer of support units 10 occurs only from one source string at a time.

Figure 8:
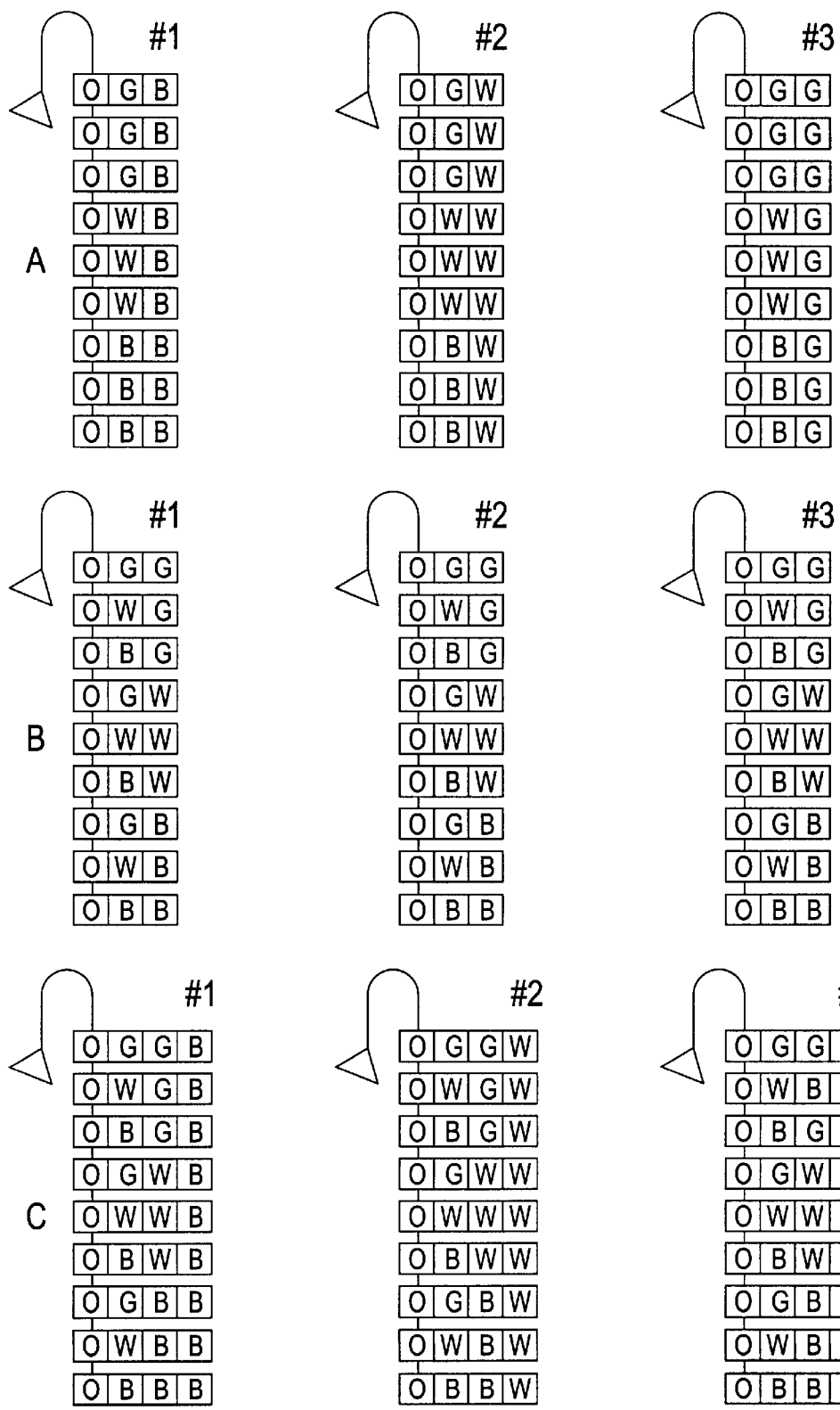
FIG. 8 is schematic representation showing the support unit strings of FIG. 7 after the subsequent coupling reactions and serial sorts.

Referring to FIG. 7 AND FIG. 8, serial sorting is illustrated in more detail in the production of a library of trimers in which the support units 10 are symbolized by rectangles and the various coupled monomers by rectangles labled B, W and G. From the three monomers, 27 trimers are prepared. At the beginning, the 27 support units 10 are placed on 3 strings (S1, S2, S3), 9 support units 10 on each. Strings S1, S2 and S3 are first placed into three reaction vessels for coupling with the B, W and G monomers, respectively. The three strings after coupling become source strings 48 as shown in FIG. 7. A single monomer species is coupled to each support unit 10 of the source string 48 and the species is different for each string. To the support units 10 of S1 string, for example, only the B monomer is attached. Prior to the second coupling step, the support units 10 of the source strings, S1, S2 and S3, are distributed to the destination strings 50 labled D1, D2 and D3. The arrows in FIG. 7 illustrate the serial sort distribution pattern of the source strings 48 of support units 10 to the destination strings 50. First, the full content of string S1 is transferred in transfer blocks of three support units each onto the destination strings D1, D2 and D3. Then follows the sequential transfer of the support units 10 from source string S2 and finaly from source string S3. Although, as illustrated, only one S1, S2 and S3 string is used it will be understood that depending on the equipment and the quantity of final product to be synthesized, the number of strings may be doubled, tripled and the like so long as the relationship of the number of strings to the number of reaction steps remains constant.

The number of support units 10 in a transfer block is calculated by dividing the number of identical support units of a source string 48 by the number of the destination strings 50. Since there are 9 identical support units 10 on each of the source strings 48 (S1, S2 and S3), this number is divided by 3, the number of destination strings 50 (D1, D2 and D3) so the transfer blocks in the illustration contain three support units.

Next, the strings D1, D2 and D3 are subjected to a reaction step in separate reaction vessels to couple the B, W and G monomers onto the monomers from the first reaction step and these strings now become the source strings 48 for the next sorting step. The result is demonstrated in FIG. 8 (row A) where the destination strings 50 from FIG. 7 now have two monomers coupled on the each support unit 10. The support units 10 are resorted serially to row B as a transfer block of one support unit because on the strings of row A there are only 3 identical support units which have to be distributed among the 3 destination strings 50 of row B. First, all support units 10 of the #1 source string (row A) are distributed among the #1, #2 and #3 destination strings 50 of row B (sorting begins with deliveries from the bottom of the source string to the bottom of the destination strings). Then the support units 10 of string #2/A, and after that the support units of string #3/A are distributed. As a result of the above described redistribution, the distribution of intermediate products on the three destination strings 50 (row B), as required by the principles of split synthesis, is exactly the same. Next, each of these strings are coupled with one of the three monomers (B, W and G squares). As a result, the content of the three strings becomes different (row C) and the coupled product of each of the 27 support units 10 is different. The distribution of the products in the support units 10 is strictly defined by the distribution pattern which makes it possible to predict the unique product structure of each support unit without tagging or otherwise analysing the compounds on the supports.

As shown schematically in FIG. 6, in parallel sorting, the source strings 48 are aligned with the destination strings 50 and deliveries of the support units 10 are executed in parallel from each source string to the corresponding aligned destination string. The alignment is then changed and the next set of support units 10 are transferred from each source string to the aligned destination string. Parallel sorting is the most efficient sorting technique to be used when the number of source strings 48 equals the number of destination strings. Preferably the strings are circularly arranged, for example on a carousel, which allows either the source strings 48 or the destination strings 50 to be rotated into a new alignment after each transfer of the support units.

In semi-parallel sorting, illustrated schematically in FIG. 6, the deliveries of transfer groups of support units 10 also start with one source string. As the destination strings 5 are repositioned into alignment with the source strings, transfer blocks are transferred from each of the source strings 48 that are aligned with a destination string. As illustrated in FIG. 6 the destination strings 50 move right to left. There are five transfer positions in the illustration, i.e.(i) the right source string 48 aligned with the left destination string 50; (ii) the right and center source strings aligned with the left and the center destination strings; (iii) all three source strings aligned with all three destination strings; (iv) the left and the center source strings aligned with the center and the right destination strings; and (v) the left source string aligned with the right destination string. Accordingly, transfers can occur from one, two or three source strings 48 in a single position. For this reason semi-parallel sorting is more efficient than serial sorting where transfer of support units 10 occurs only from one source string at a time.

Figure 9:
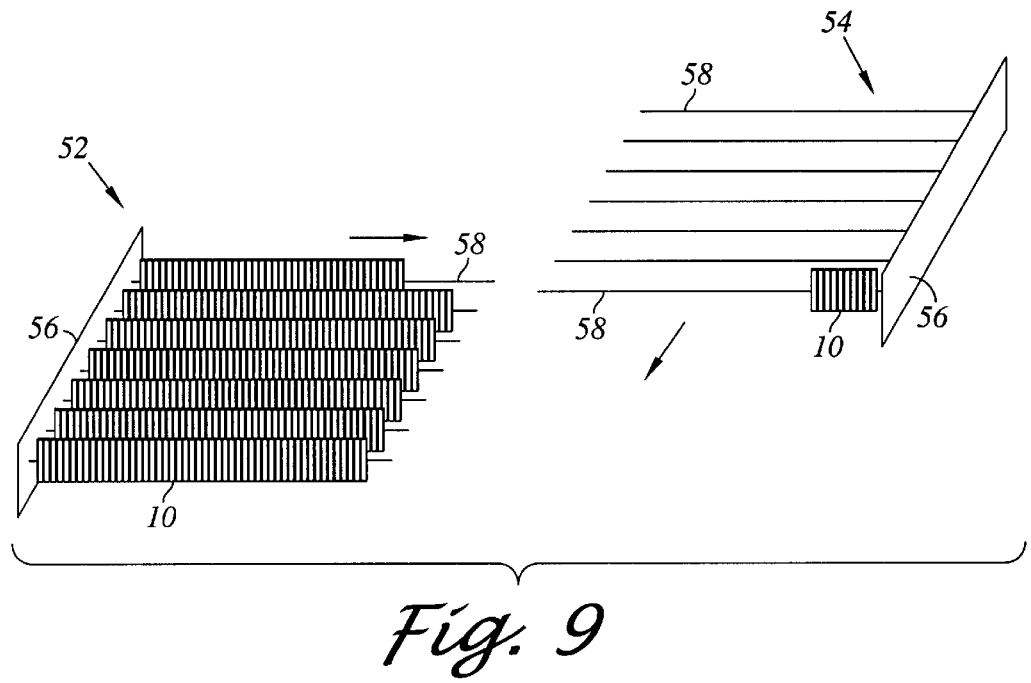
FIG. 9 illustrates a simple device for sorting support units in accordance with the method of the present invention.

As mentioned above, sorting the support units 10 can be done manually or with automated equipment. FIG. 9 illustrates an example of manual sorting apparatus comprising a source rack 52 and a destination rack 54. The source rack 52 consists of a lateral member 56 from which a series of rods 58 extend. The disk shaped support units 10 are carried on the rods 58 which extend through the center holes of the support units. The destination rack 54 corresponds to the source rack 52 in its construction and at least an equal number of rods 58 extend from the lateral member. The spacing between the rods 58 is at least double the radius of the support disks, and is preferably greater, so that the support units 10 on adjacent rods 58 can be freely moved without binding against adjacent support units. As illustrated, the first rod 58 of the source rack 52 is aligned with the first rod of the destination rack 54 and the desired number of support units 10 is moved onto the rod of the destination rack. The destination rack 54 is moved so that its second rod 58 is aligned with the first rod of the source rack 52 for transfer of a block of support units 10. At the same time the first rod 58 of the destination rack 54 is aligned with the second rod of the source rack 52 and a block of support units 10 is transferred to the destination rack. This procedure is carried out until all blocks of the support units 10 have been transferred from the source rack 52 to the destination rack. The source rack 52 and the destination rack 54 can be adapted so that the sorting operation can be carried out by robotic equipment or other automated equipment. In the illustration, the destination rack 54 moved generally in a direction from the top of the illustration toward the bottom. However, it will be understood that the direction of travel of either the destination rack 54 or the source rack 52 is not critical as long as the orientation of the strings and the direction of travel reflected in the software tracking the position of the support units 10.

Figure 10:
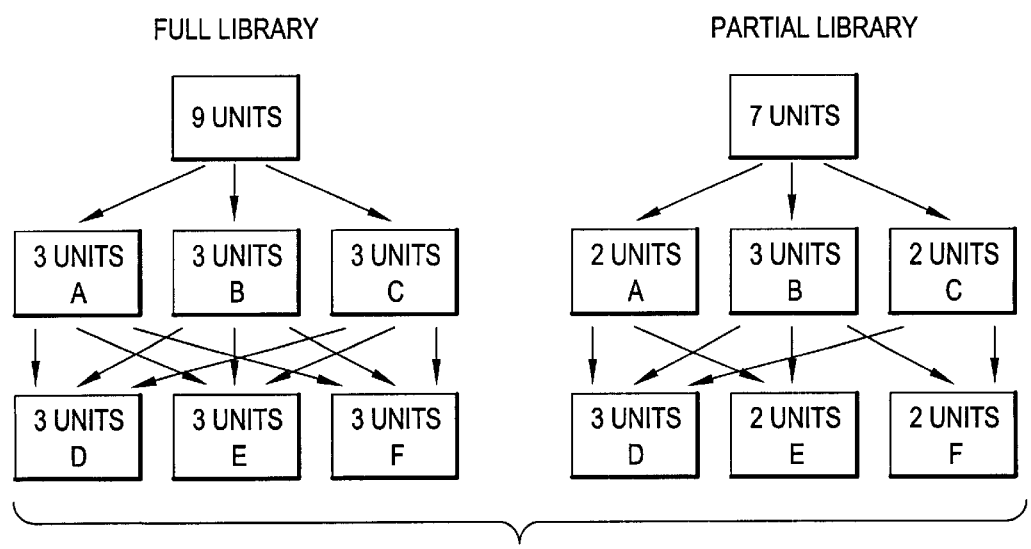
FIG. 10 is a schematic representation of a reaction and serial sort sequence to produce a full combinatorial library and a partial combinatorial library.

The split synthesis technique normally produces every structural variation that can be produced from the monomers used in the reaction steps. Thus, using 9 monomers in each of three coupling steps one can expect to produce a library consisting of 727 different trimer structures. However, in some cases it may be desired to eliminate certain unwanted structures from the library. Accordingly, using the method of the invention the unwanted structures are eliminated by reducing the number of monomers used in the reactions to eliminate the unwanted monomers. For example as shown in FIG. 10A there is schematically illustrated the simple case of producing a library of dimers according to the method of the invention using the monomers A, B and C in the first reaction step, sorted as illustrated by the arrows and then coupled with D, E and F in the second reaction step of the expected structures AD, AE, AF, BD, BE, BF, CD, CE and CF. The source strings carry 3 support units. For example, if the structures AF and CE are unwanted, the support units 10 can be reduced to 7 units. As shown in FIG. 10B, 2 units are positioned on the left and right strings and 3 units on the center string. The strings are reacted and sorted as illustrated by the arrows and subjected to a second coupling step to produce the structures AD, AE, BD, BE, BF, CD and CF. The location of the strings and the number of support units on the strings can be varied to control the number and the structure of the compounds produced.

The whole sorting process is preferably controlled by a computer which keeps track of the position history of each support unit 10. The computer also stores a record for each synthesized compound. This includes the number of the string on which its support unit 10 is found as well as the position occupied by the support unit on the string.

EXAMPLES

Example 1

Figure 11:
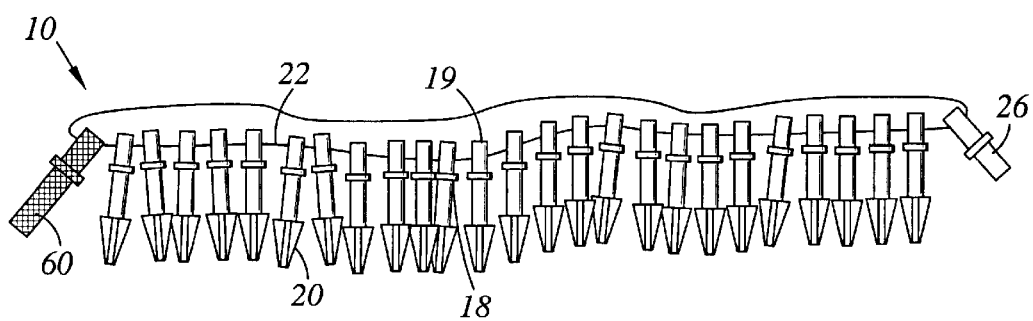
FIG. 11 illustrates a string of crown stems.

As an example, a 125 member tripeptide library is prepared using resin crowns 20 as the solid supports 10. As illustrated in FIG. 11 the crown stems 18 were provided with hangers 19 having through running holes for arranging the crowns in 5 strings of 25 crowns each on polyethylene fishing line retainers 22. The holes faced each other to facilitate stringing and the head 30 of each string was tagged with a full stem 60 to identify the string and to insure that the orientation of the support unit sequence was maintained during each coupling and sorting step. The stems were colored red, yellow, green, blue and black for strings 1, 2, 3, 4 and 5, respectively. Each string was placed in a separate reaction flask for treatment of the crowns to couple a protected amino acid on the crowns. Fmoc-Phe was coupled on string 1, Fmoc-Gly on string 2, Fmoc-Leu on string 3, Fmoc-Ile on string 4 and Fmoc-Val on string 5.

Example 2

First Semi-parallel Sorting of the Crowns

Figure 12:
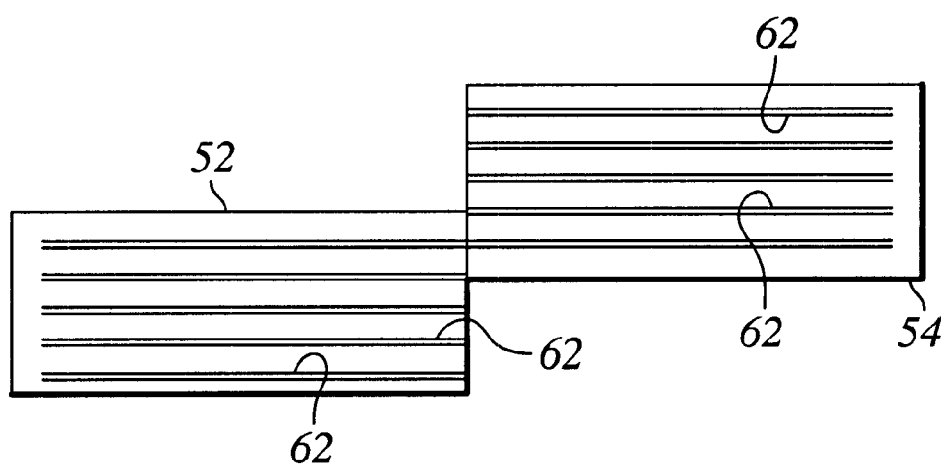
FIG. 12 illustrates a manual sorting device.

To facilitate the sorting operation a simple two piece manual sorting device consisting of a source rack 52 and a destination rack 54 was made from slotted aluminum trays (FIG. 12). The source rack 52 was provided with 5 equally spaced apart parallel slots 62 that, for purposes of description are called source slots. The destination rack was similarly provided with 5 spaced apart parallel slots 62 called destination slots for purposes of description. During the sorting operations described herein, the destination rack 54 was moved laterally from right to left with respect to the source rack 52 (as illustrated from the upper towards the lower portion of the drawing) to align the source and destination slots in 9 different sorting positions. The crowns were placed into the slots 62 of the source rack 52 as shown in FIG. 11 and moved along the slots into the appropriate aligned destination slots of the destination rack 54.

The 5 strings from Example 1 were placed into the source slots 62 of the source rack 52. The crowns coupled with Fmoc-Phe, Fmoc-Gly, Fmoc-Leu, Fmoc-Ile and Fmoc-Val were placed into source slots 1, 2, 3, 4, and 5, respectively. Sorting was carried out in accordance with the semi-parallel protocol described above and illustrated in FIG. 6 by transferring blocks of five crowns each into the destination slots 62 of the destination rack 54 as they were moved into alignment with the source slots. The colored stems from the source strings were placed in the corresponding destination slots at the head of the strings. The destination strings 50 were labeled with red, yellow, green, blue and black tags corresponding to the color of the source string to identify the strings and to insure the correct orientation of the support units 10 during the next sorting step. After sorting, a polyethylene line was inserted through the stem holes in the hangers crowns of each destination slot and the ends looped back and tied together.

Example 3

Coupling the Second Amino Acid to the Crowns

After sorting, the red, yellow, green, blue and black labeled strings were placed into reaction flasks to couple Fmoc-Glu, Fmoc-Trp, Fmoc-Phe, Fmoc-Ser and Fmoc-Tyr, respectively on the crowns of the support units 10 of the respective strings.

Example 4

Second Sorting

The strings labled with red, yellow, green, blue and black colored stems were replaced in the source rack slots 1, 2, 3, 4 and 5 respectively and the flexible cord was cut and removed. Sorting was conducted according to semi-parallel protocol as in Example 2 except that the transfer groups consisted of single support units. At the completion of the first sorting pass 5 units were transferred to each of the destination slots. The destination rack 54 was returned to its original position and the transfer was repeated as in the first pass. A total of five sorting passes were required to transfer all of the support units.

Example 5

Coupling the Third Amino Acid to the Crowns

The strings from Example 4 were placed into reaction flasks and submitted to coupling as described in Example 3. The software developed to trace the crowns in semi-parallel sorting was used to predict the tripeptide sequences formed on the 125 crowns. Table 1 shows the sequences depending on the position of the crowns occupied on the five strings.

Example 6

Confirmation of the Sequences of 5 Randomly Selected Tripeptide

In order to confirm the tripeptide sequence predictions for the compounds formed in Example 1–4, one crown was randomly selected from each string to compare its experimentally determined sequence with the predicted one. The selected crowns and their positions, as well as the sequences they carry, are shown in bold type in Table 1 below. The five tripeptides were independently synthesized and their HPLC retention times were compared to those of the peptides formed on the crowns. The predicted sequences conformed to the sequences of the tripeptide that were analyzed.

TABLE 1

Predicted positions or the synthesized tripeptide on the five strings

| No. | Str1 | Str2 | Str3 | Str4 | Str5 |
|---|---|---|---|---|---|
| 1 | EEF | WEF | FEF | SEF | YEF |
| 2 | EWF | WWF | FWF | SWF | YWF |
| 3 | EFF | WFF | FFF | SFF | YFF |
| 4 | ESF | WSF | FSF | 5SF | YSF |
| 5 | EYF | WYF | FYF | SYF | YYF |
| 6 | EEG | WEG | FEG | SEG | YEG |
| 7 | EWG | WWG | FWG | SWG | YWG |
| 8 | EFG | WFG | FFG | SFG | YFG |
| 9 | ESG | WSG | FSG | SSG | YSG |
| 10 | EYG | WYG | FYG | SYG | YYG |
| 11 | EEL | WEL | FEL | SEL | YEL |
| 12 | EWL | WWL | FWL | SWL | YWL |
| 13 | EFL | WFL | FFL | SFL | YFL |
| 14 | ESL | WSL | FSL | SSL | YSL |
| 15 | EYL | WYL | FYL | SYL | YYL |
| 16 | EEI | WEI | FEI | SEI | YEI |
| 17 | EWI | WWI | FWI | SWI | YWI |
| 18 | EFI | WFI | FFI | SFI | YFI |
| 19 | ESI | WSI | FSI | SSI | YSI |
| 20 | EYI | WYI | FYI | SYI | YYI |
| 21 | EEV | WEV | FEV | SEV | YEV |
| 22 | EWV | WWV | FWV | SWV | YWV |
| 23 | EFV | WFV | FFV | SFV | YFV |
| 24 | ESV | WSV | FSV | SSV | YSV |
| 25 | EYV | WYV | FYV | SYY | YYV |

F: Phe,
O: Oly,
L: Len,
I: Ile,
V: Val,
E: Olu,
W: Trp,
S: Ser,
Y: Tyr

The present invention provides very fast sorting which can be attributed to several factors. Since there are no codes, no time is lost in code reading. By virtue of the history of the spatial location of each support unit 10 during the reaction steps, the composition of each compound is predicted and the time consuming sequencing analysis is avoided. The fast sorting of support units introduced in this invention removes the time barrier in redistribution of support units in the split synthesis and, facilitates the application of this very efficient method for the preparation of individual compounds in large quantities as preferred in the pharmaceutical research.

As will be understood by those skilled in the art, various arrangements which lie within the spirit and scope of the invention other than those described in detail in the specification will occur to those persons skilled in the art. It is therefor to be understood that the invention is to be limited only by the claims appended hereto.

Having described the invention, I claim:

1. A method for the solid support synthesis of combinatorial libraries using a split technique comprising the steps of:
    a. forming at least two strings of solid support units comprising a sequence of spatially arranged solid support units secured by a retainer for maintaining the sequential arrangement of said support units in said strings, said support units having surface for coupling a first product segment;
    b. converting said strings to source strings by coupling a first product segment on the support units of said source strings, the first product segment on each of the source strings being different;
    c. transferring said support units in a predetermined pattern from each source string to destination string retainers to form a corresponding number of destination strings in which the support units from said source strings are disposed in a new sequential arrangement on said destination strings;
    d. determining the sequential position of each of said support units on said destination strings;
whereby the position history of each support unit allows the structure of each product produced on each support unit to be predicted and the need for labels is eliminated.

2. The method of claim 1 wherein a minimum total number of support units on a string of support units is equal to the number of compounds to be prepared.

3. The method of claim 1 wherein the number of strings of support units is determined by the number of different product segments in the finished products to be formed.

4. The method of claim 1 wherein each string of support units is distinctly marked for identification and to indicate a head and a tail for said support unit sequence.

5. The method of claim 1 wherein the support units of a source string are rearranged on destination string retainers by sequentially transferring at least one of the support units from a first source string to each of said destination string retainers until all support units on said first source string have been transferred followed by sequentially transferring at least one of the support units from a second source string to each of said destination strings, said transfers of the support units being carried out until all of the support units of said source strings have been transferred to corresponding destination strings.

6. The method of claim 5 wherein the support units are transferred in blocks of support units determined by dividing the number of support units of a source string on which are coupled identical product sequences by the number of destination strings.

7. The method of claim 1 wherein each of said source strings of support units is matched with a corresponding destination string retainer, at least one of the support units of each of said source strings is moved onto said corresponding destination string retainer, thereafter said source strings are rematched with a different destination string retainer and at least one support unit from each of said source strings is moved to said corresponding destination string retainer, said source string and destination string retainer rematching and support unit movement steps being repeated until all support units have been moved from said source strings to said destination string retainers thereby to form destination strings of support units.

8. The method of claim 7 wherein said source strings of support units and said destination string retainers are disposed on a carousel so that said source strings can be rotated with respect to said destination string retainers to rematch said source strings and said destination string retainers.

9. The method of claim 1 wherein a first source string of support units is matched with a first destination string retainer and at least one support unit is transferred from said first source string to said first destination string retainer, thereafter rematching said first source string with a second destination string retainer and a second source string with said first destination string retainer and moving at least one support unit from said first source string to said second destination string retainer and from said second source string to said first destination string retainer, said rematching step and said support unit moving step being repeated until all of said source strings have been matched with all of said destination string retainers and all of the support units have been transferred to form destination strings.

10. The method of claim 1 wherein the orientation of said sequence of support units on said strings of support units remains the same during all of said sorting steps so that the order of transfer of support units in said sequence on each said string is the same for each sorting step.

11. The method of claim 1 wherein said destination strings of support units are converted to source strings of support units by coupling a second product segment to said first product segment and thereafter repeating steps c and d.

12. The method of claim 11 wherein the step of converting said destination strings of support units to source strings of support units and steps c and d are repeated until products of desired sequences are formed.

* * * * *